(12) United States Patent
Hwang et al.

(10) Patent No.: US 11,293,055 B2
(45) Date of Patent: Apr. 5, 2022

(54) NUCLEIC ACID DETECTION KIT AND NUCLEIC ACID DETECTION METHOD USING NANOPARTICLES

(71) Applicant: NATIONAL CANCER CENTER, Goyang-si (KR)

(72) Inventors: Sang Hyun Hwang, Seoul (KR); Ji Hyun Lim, Incheon (KR); Su Jin Gang, Incheon (KR); Do Hoon Lee, Goyang-si (KR)

(73) Assignee: NATIONAL CANCER CENTER, Goyang-si (KR)

( * ) Notice: Subject to any disclaimer, the term of this patent is extended or adjusted under 35 U.S.C. 154(b) by 0 days.

(21) Appl. No.: 15/744,353

(22) PCT Filed: Jul. 22, 2016

(86) PCT No.: PCT/KR2016/008047
§ 371 (c)(1),
(2) Date: Jan. 12, 2018

(87) PCT Pub. No.: WO2017/010854
PCT Pub. Date: Jan. 19, 2017

(65) Prior Publication Data
US 2018/0201986 A1   Jul. 19, 2018

(30) Foreign Application Priority Data

Jul. 13, 2015 (KR) .................. 10-2015-0099378
Aug. 27, 2015 (KR) .................. 10-2015-0121109

(51) Int. Cl.
*C12Q 1/6848* (2018.01)
*C12Q 1/6816* (2018.01)
*C12Q 1/686* (2018.01)
*C12Q 1/6876* (2018.01)

(52) U.S. Cl.
CPC ......... *C12Q 1/6848* (2013.01); *C12Q 1/6816* (2013.01); *C12Q 1/686* (2013.01); *C12Q 1/6876* (2013.01)

(58) Field of Classification Search
CPC ............ C12Q 2563/155; C12Q 1/6816; C12Q 1/6848; C12Q 1/686; C12Q 1/6876; C12Q 2565/519; C12Q 1/68
See application file for complete search history.

(56) References Cited

U.S. PATENT DOCUMENTS

| | | | | |
|---|---|---|---|---|
| 5,914,230 A | * | 6/1999 | Liu | C12Q 1/6813 435/6.1 |
| 2001/0036634 A1 | * | 11/2001 | Chow | B01L 3/5023 435/6.12 |
| 2010/0009383 A1 | | 1/2010 | Kiesewetter et al. | |
| 2012/0028344 A1 | | 2/2012 | Chiapperi et al. | |
| 2014/0100131 A1 | | 4/2014 | Gao et al. | |

FOREIGN PATENT DOCUMENTS

| JP | 2005-000162 A | 1/2005 |
|---|---|---|
| JP | 2014-515601 A | 7/2014 |
| KR | 10-0771554 B1 | 11/2007 |
| KR | 10-2012-0054882 A | 5/2012 |
| KR | 10-1397793 B1 | 5/2014 |
| WO | 99/50673 A1 | 10/1999 |

OTHER PUBLICATIONS

Hwang et al., "Rapid visual identification of PCR amplified nucleic acids by centrifugal gel separation: Potential use for molecular point-of-care tests," Biosensors and Bioelectronics, vol. 79, pp. 829-834. (Year: 2016).*
Schonemann et al., "Application of the particle gel agglutination system as a new check gel assay for PCR products," International Journal of Immunogenetics, vol. 34, pp. 337-339. (Year: 2007).*
Schmidt, B.L., "Evaluation of a New Particle Gel Immunoassay for Determination of Antibodies against Treponema pallidum," Journal of Clinical Microbiology, June, vol. 42, No. 6, pp. 2833-2835. (Year: 2004).*
Hwang et al., "Rapid visual identification of PCR amplified nucleic acids by centrifugal gel separation: Potential use for molecular point-of-care tests," Biosensors and Bioelectronics, Jan. 5, vol. 79, pp. 829-834. (Year: 2016).*
International Search Report for PCT/KR2016/008047, dated Dec. 1, 2016.

* cited by examiner

*Primary Examiner* — Young J Kim
(74) *Attorney, Agent, or Firm* — Sughrue Mion, PLLC (57) ABSTRACT

The present invention relates to a nucleic acid detection kit and a nucleic acid detection method, which use nanoparticles. More specifically, the present invention relates to: a nucleic acid detection method comprising a step of amplifying and labeling nucleic acids, and then capturing the same by using nanoparticles and centrifuging the same; and a nucleic acid detection kit using the method. The present invention is effective since a negative or positive determination for a particular disease can be made, through the nucleic acid detection method not comprising a separation step, in a more rapid, simple, sensitive, and highly reliable manner.

8 Claims, 8 Drawing Sheets

Specification includes a Sequence Listing.

Lane M : 100bp ladder
Lane 1 : NTC b-c
Lane 2 : standard DNA HPV16 $10^5$ copies/mL (No.3 of gel image below)
Lane 3 : standard DNA HPV16 $10^4$ copies/mL (No.4 of gel image below)
Lane 4 : standard DNA HPV16 $10^3$ copies/mL (No.5 of gel image below)
Lane 5 : standard DNA HPV16 $10^2$ copies/mL (No.6 of gel image below)

FIG. 8

NUCLEIC ACID DETECTION KIT AND NUCLEIC ACID DETECTION METHOD USING NANOPARTICLES

This application is a National Stage of International Application No. PCT/KR2016/008047 filed Jul. 22, 2016, claiming priority based on Korean Patent Application No. 10-2015-0099378, filed on Jul. 13, 2015, and Korean Patent Application No. 10-2015-0121109, filed on Aug. 27, 2015, the disclosures of which are incorporated herein by reference in their entireties.

TECHNICAL FIELD

This application claims priority to and the benefits of Korean Patent Application No. 10-2015-0099378, filed on Jul. 13, 2015, and Korean Patent Application No. 10-2015-0121109, filed on Aug. 27, 2015, the disclosures of which are incorporated herein by reference in their entireties.

The present invention relates to a kit for detecting a nucleic acid using nanoparticles and a method for detecting a nucleic acid, and more particularly, to a method for detecting a nucleic acid which includes amplifying and labeling a nucleic acid, capturing it with nanoparticles, and performing centrifugation, and a kit for detecting a nucleic acid using the method.

BACKGROUND ART

The necessity of an ultra-high speed nucleic acid test is increasing in many fields. A nucleic acid test is used to ultimately reduce overall medical expenses by early detection of a disease, and a demand for simultaneous analysis of various types of nucleic acids for the future pathogen tests, xenotyping and cancer diagnosis, and a demand for products that can be used for point-of-care testing are expected to rapidly increase. To achieve these, DNA/RNA labels with high specificity and sensitivity with respect to xenotyping and cancer diagnosis should be developed a lot. While there are many problems that should be solved so that the nucleic acid test is widely used, it is only a matter of time until the nucleic acid test is expected to dominate the diagnostic market soon. To accelerate the time, the development of a device for a low-cost nucleic acid test and efficient DNA labels has become the focus of research.

The nucleic acid test should satisfy analytical validities such as sensitivity, specificity, precision and accuracy, and clinical validities such as clinical sensitivity and specificity, a negative predictive value and clinical utility. Targets for the nucleic acid test are largely divided into two types: nucleic acids derived from microorganisms infecting a human body and nucleic acids directly derived from a human body. The former is detected by a test for diagnosing infections, which accounts for more than 80% of the market. The latter is detected by a genetic test for analyzing nucleic acids related to the occurrence and treatment of a disease, which accounts for less than 20% in the market, but is expected to have very high potential value and marketability.

Among various methods for detecting a nucleic acid, nucleic acid detection using nanoparticles is a next generation technique, which can dramatically improve disadvantages of conventional methods, such as a low speed and high costs, using a negative-charged polyanion resin and a silica membrane technique, and systems for detecting nucleic acids by preparing nanoparticles, and selectively binding a target nucleic acid molecule by performing coating treatment for capturing a nucleic acid are being competitively developed. As prior art documents, there are U.S. Patent No. US20140100131, relating to a method for detecting a target gene using magnetic beads, and U.S. Patent No. US20100009383, relating to a method for detecting a target biomolecule, and after a target substance is collected using magnetic beads, an agglomerated target substance may be detected by centrifugation. However, the conventional methods are inconvenient due to additional DNA probes or antibodies, and additionally need separation and washing steps, and therefore a novel invention relating to a more rapid nucleic acid detection method was needed.

Therefore, the inventors manufactured a gel card using an amplified target nucleic acid and nanoparticles, demonstrated that the target nucleic acid can be observed visually or by fluorescence analysis after centrifugation, and confirmed that such a nucleic acid detection method has a significant effect of detecting a specific nucleic acid for a specific disease. Accordingly, the present invention provides a method for detecting a nucleic acid and a kit for detecting a nucleic acid, which can make a negative or positive determination for a specific disease in a more rapid, simple, and highly sensitive and reliable manner through a nucleic acid detection method not including a separation step.

DISCLOSURE

Technical Problem

The present invention is directed to providing a kit for rapidly and accurately detecting a nucleic acid.

The present invention is also directed to providing a nanoparticle complex for detecting a nucleic acid.

The present invention is also directed to providing a gel card for detecting a nanoparticle complex.

The present invention is also directed to providing a method for rapidly and accurately detecting a nucleic acid.

Technical Solution

To achieve the objects of the present invention, the present invention provides a kit for detecting a nucleic acid, which includes a primer set specifically binding to a nucleic acid to be detected; capture nanoparticles; and a gel card in which a component generating a density difference and a gel component are sequentially stacked.

The present invention also provides a detectable nanoparticle complex which includes target nucleic acid-capturing or binding nanoparticles to be used in an assay for detecting a target nucleic acid.

The present invention also provides a gel card in which a glass bead component and a gel component are sequentially stacked to detect a nanoparticle complex.

The present invention also provides a use of a detectable nanoparticle complex, which includes target nucleic acid-capturing or binding nanoparticles to be used in an assay for detecting a target nucleic acid.

The present invention also provides a use of a gel card in which a glass bead component and a gel component are sequentially stacked to detect the nanoparticle complex.

The present invention also provides a method for detecting a nucleic acid using nanoparticles, which includes: (a) amplifying a target nucleic acid using a primer set specifically binding to a target nucleic acid; (b) adding nanoparticles to the amplified nucleic acid obtained in Step (a) to allow the nucleic acid to be captured by or bind to the nanoparticles; (c) putting the complex obtained by capturing the nucleic acid by the nanoparticles or binding the nucleic acid to the nanoparticles as described in Step (b) into a gel card container; (d) centrifuging the mixture prepared in Step (c); and (e) comparing a location of a precipitate in the gel card container with a control.

According to an exemplary embodiment of the present invention, the primer set in Step (a) may include a biotin-labeled forward primer and a fluorescence-labeled reverse primer.

According to another exemplary embodiment of the present invention, Step (a) may be a step of amplifying a nucleic acid by polymerase chain reaction (PCR) or an isothermal amplification reaction.

The isothermal amplification reaction may be performed by any one method selected from the group consisting of Helicase-Dependent Amplification (HDA), Recombinase Polymerase Amplification (RPA), Rolling Circle Amplification (RCA), Loop mediated isothermal amplification (LAMP), Nucleic Acid Sequence-Based Amplification (NASBA), Transcription Mediated Amplification (TMA), Signal Mediated Amplification of RNA Technology (SMART), Strand Displacement Amplification (SDA), Isothermal Multiple Displacement Amplification (IMDA), Single Primer Isothermal Amplification (SPIA) and circular Helicase-Dependent Amplification (cHDA), and preferably HDA, RPA, RCA, or LAMP, and more preferably, HDA or RPA.

According to still another exemplary embodiment of the present invention, the nanoparticles of the present invention may be any one selected from the group consisting of magnetic beads, gold (Au) nanoparticles, silver (Ag) nanoparticles, platinum (Pt) nanoparticles, quantum dots, upconversion nanoparticles (UCNP), a graphene-nanoparticle complex, color dyed particles and latex nanoparticles.

In addition, a surface of the nanoparticles of the present invention may be coated with any one selected from the group consisting of avidin, amine and streptavidin, which are able to capture a nucleic acid, an antibody (e.g., an equivalent such as a digoxigenin/anti-digoxigenin antibody or a Cy3/anti-Cy3 antibody), which can bind to a primer-binding antigen through an antigen-antibody reaction, an aptamer and an oligonucleotide.

In the present invention, the gel component may be any one selected from the group consisting of IgG-agarose, agarose, agar, cellulose acetate and a polyacrylamide gel.

The method for detecting a nucleic acid may further include treating an enhancer, and does not need separation and washing steps included in a conventional method.

Advantageous Effects

The present invention relates to a kit for detecting a nucleic acid and a method for detecting a nucleic acid, and more particularly, a method for detecting a nucleic acid including amplifying and labeling a nucleic acid, capturing it with nanoparticles, and performing centrifugation, and a kit for detecting a nucleic acid. The present invention is effective since a negative or positive determination for a specific disease can be made in a more rapid, simple, and highly sensitive and reliable manner through a nucleic acid detection method not including a separation step.

MODES OF THE INVENTION

Hereinafter, the present invention will be described in further detail.

As described above, a conventional negative and positive determination for a disease-related specific nucleic acid generally takes a long time, for example, 4 to 6 hours, and has low accuracy. Therefore, it is difficult to give a prompt prescription to a positive patient.

In addition, in U.S. Patent Application Publication No. 2014-0100131 relating to a method for detecting a target gene, an antibody is used, only magnetic beads should be used as nanoparticles, and a separation step is additionally used. For this reason, rapid detection is difficult.

Therefore, the inventors invented a method for rapidly and accurately detecting a disease-specific nucleic acid by a simple method of amplifying a target nucleic acid, injecting it into a gel card with nanoparticles and a gel component, and performing centrifugation.

Terms used in the present invention are defined as follows.

The term "nucleic acid" used herein refers to a polymer of nucleotides with an arbitrary length, and includes DNA and RNA.

The "capturing" or "binding" used herein may refer to binding or fixing at least a part of one or more preparations (or a linker binding to the preparation) to nanoparticles or a surface thereof through scavenging, adsorption, electrostatic coupling, ionic bonding, covalent bonding, complementary oligonucleotide bonding, or coupling by an antigen-antibody reaction.

The "primer" used herein refers to an oligonucleotide, and may act as a starting point of synthesis under conditions of inducing the synthesis of a primer elongation product complementary to a nucleic acid chain (template), that is, in the presence of polymerases such as nucleotide and DNA polymerases, and under conditions of a suitable temperature and pH. Preferably, the primer is a deoxyribonucleotide, and a single chain. The primer used in the present invention may include a naturally-occurring dNMP (that is, dAMP, dGMP, dCMP or dTMP), a modified nucleotide, and a non-natural nucleotide. In addition, the primer may include a ribonucleotide. The primer should be long enough to prime the synthesis of an elongation product in the presence of a polymerase. A suitable length of the primer is determined by numerous factors, for example, a temperature, an application field and a source of the primer, and is typically 15 to 30 nucleotides. A short primer molecule requires generally a lower temperature to form a sufficiently stable hybrid complex with a template. The term "annealing" or "priming" refers to apposition of an oligodeoxynucleotide or nucleic acid to a template nucleic acid, and the apposition allows a template nucleic acid or a nucleic acid molecule complementary thereto to be formed by polymerizing nucleotides by means of a polymerase.

The term "enhancer" used herein refers to a material more clearly determining whether a specimen is positive or negative. For example, the enhancer may be a material that binds to a nucleic acid or primer, thereby emitting fluorescence or color.

The "gel card" may be defined with reference to a gel column disclosed in WO1999/050673. The gel card used in the present invention is a gel card in which a component generating a density difference and a gel component are sequentially stacked, and preferably an object formed by sequentially containing glass beads and an agarose gel in a container.

The present invention provides a kit for detecting a nucleic acid, which includes a primer set specifically binding to a nucleic acid to be detected; capture nanoparticles; and a gel card in which a component generating a density difference and a gel component are sequentially stacked.

The primer set may include a biotin-labeled forward primer and a fluorescence-labeled reverse primer. A primer included in the kit for detecting a nucleic acid of the present invention may be labeled with biotin, and the biotin-labeled primer is able to be more easily captured by or bound to nanoparticles, and thus the detection of a nucleic acid is facilitated. In addition, a primer included in the kit of the present invention may be labeled with fluorescence, and the fluorescence-labeled primer may determine the absence or presence of a nucleic acid according to a band position by a fluorescence assay.

Figure 6:
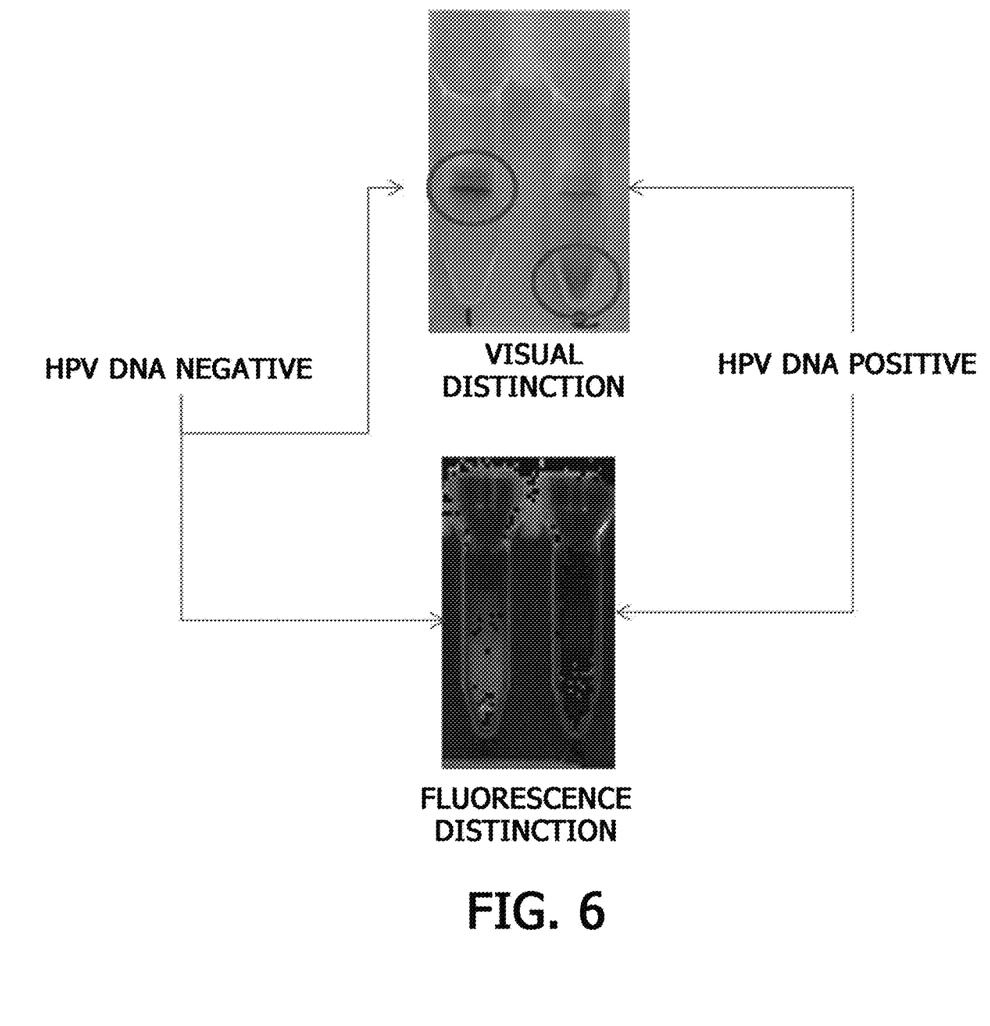
FIG. 6 shows HPV DNA nucleic acid detection results, which can be observed visually or by fluorescence analysis.

In one exemplary embodiment of the present invention, the absence or presence of a nucleic acid may be visually determined as negative or positive by labeling a primer, or using fluorescence (refer to FIG. 6).

Fluorescence labeling of the primer may be performed using any one or more selected from the group consisting of Cy3, Cy5, TAMRA, TEX, TYE, HEX, FAM, TET, JOE, MAX, ROX, VIC, Cy3.5, Texas Red, Cy5.5, TYE, BHQ, Iowa Black RQ and IRDye, but the present invention is not limited thereto.

In addition, the fluorescence labeling of the primer may be performed by two main methods such as NHS modification and phosphoramidite synthesis.

Labeling with a Cy dye may be carried out according to a method suggested in the catalog of the manufacturer Amersham Biosciences, "Labelling of oligonucleotides with CyDye fluors for fluorescent applications using the LEAD seeker homogeneous imaging system, Amersham Biosciences, Vol. L6, 2000."

In the present invention, when a nucleic acid is detected using a primer labeled by NHS modification, a positive specimen has a band at a lower position compared to a negative specimen; and when a nucleic acid is detected using a primer fluorescence-labeled by phosphoramidite synthesis, the positive specimen has a band at an upper position compared to the negative specimen. It is considered that such a difference is dependent on the position of a fluorescence label of the primer.

Figure 1:
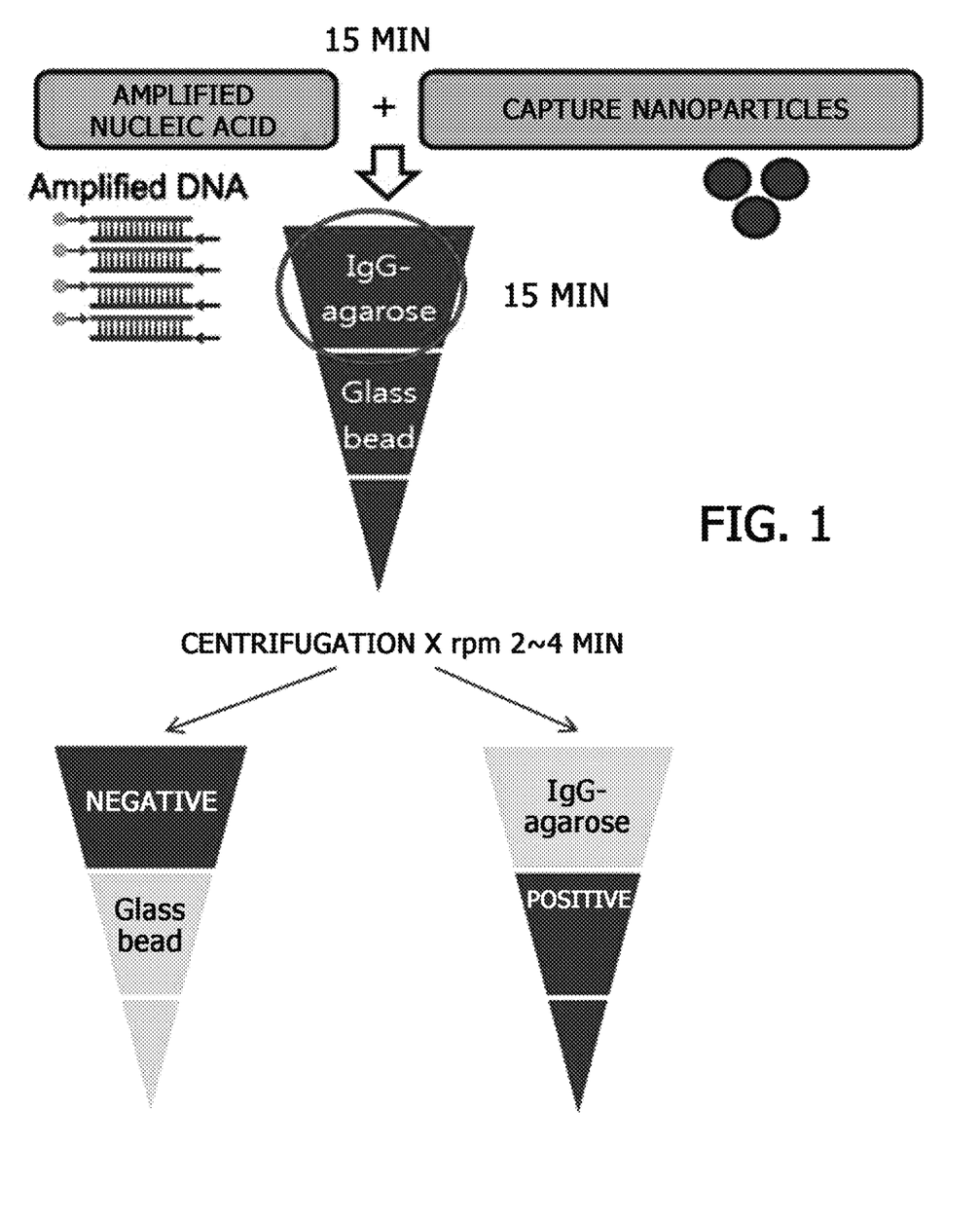
FIG. 1 is a schematic diagram illustrating a method for detecting a nucleic acid according to the present invention.
Figure 2:
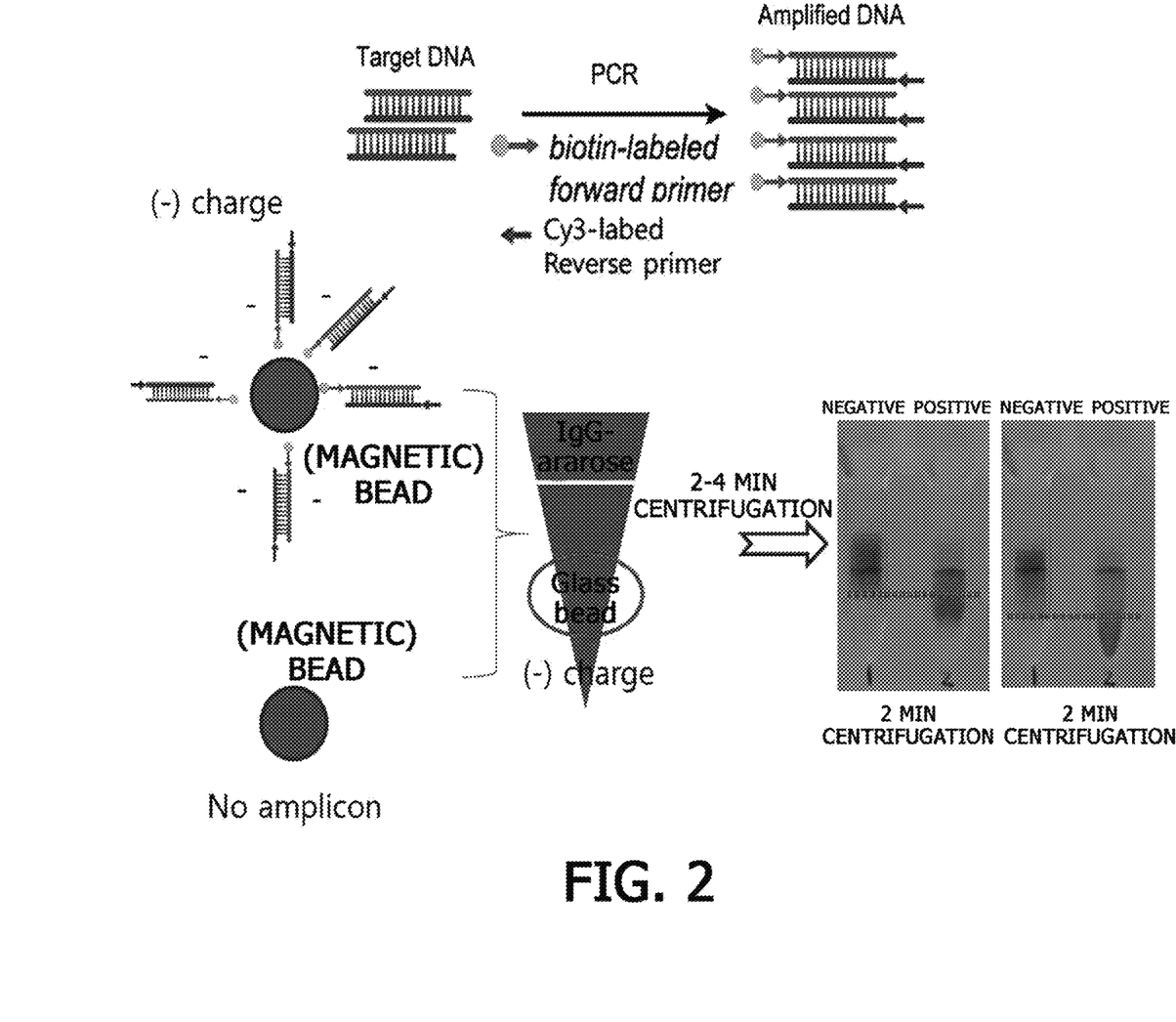
FIG. 2 shows a schematic diagram specifically illustrating the method for detecting a nucleic acid of the present invention, and images showing positive/negative results according to the method for detecting a nucleic acid using a reverse primer labeled by N-hydroxysuccinimide modification (NHS modification).
Figure 3:
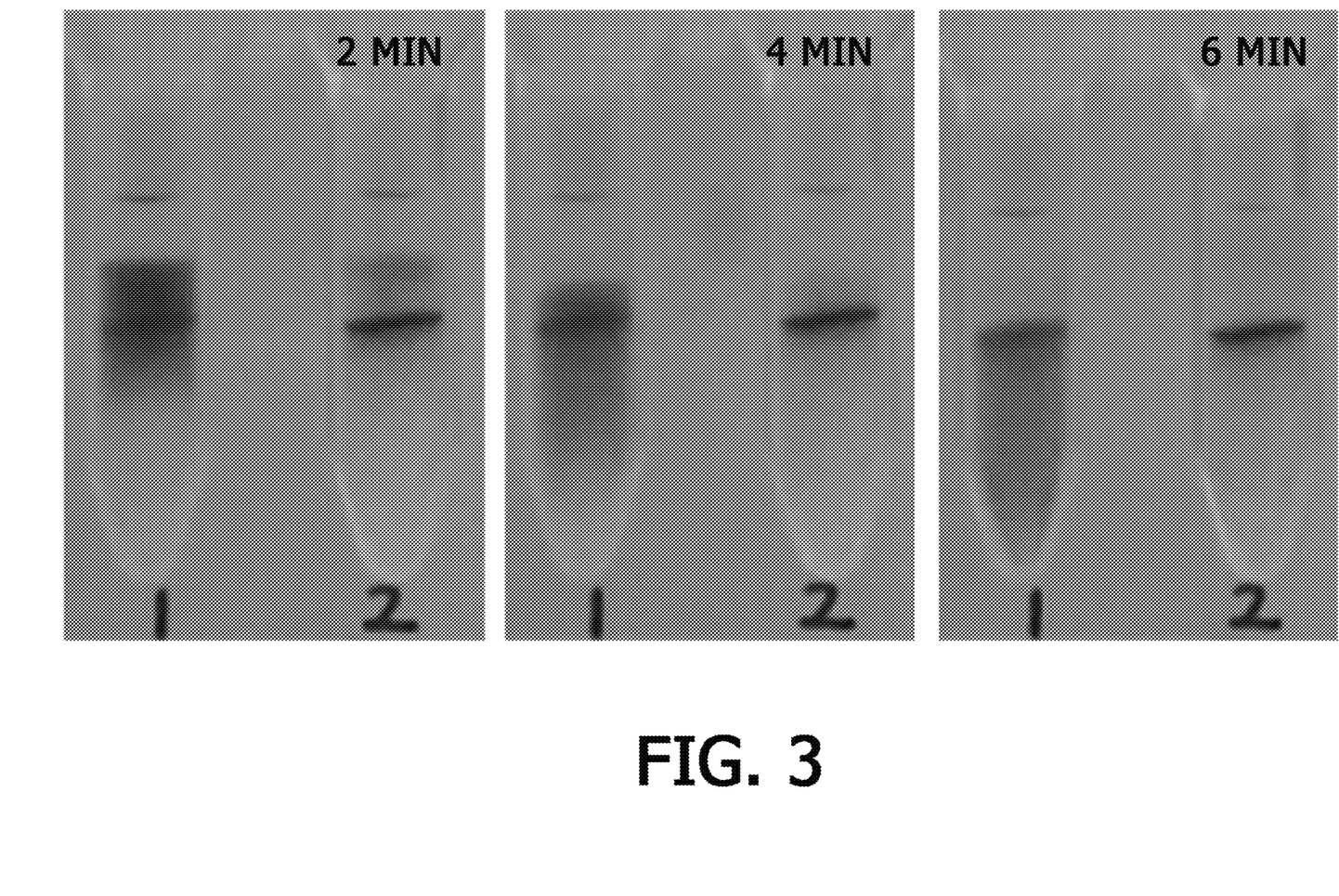
FIG. 3 show images showing positive/negative results according to the method for detecting a nucleic acid using a reverse primer labeled by phosphoramidite synthesis.

In an exemplary embodiment of the present invention, when a nucleic acid is detected using a primer fluorescence-labeled by NHS modification, a positive specimen has a band at a low position (refer to FIG. 2), and when a nucleic acid is detected using a primer fluorescence-labeled by phosphoramidite synthesis, the positive specimen has a band at an upper position (refer to FIG. 3).

The nanoparticles of the present invention may be any one selected from the group consisting of magnetic beads (magnetic bead), gold (Au) nanoparticles, silver (Ag) nanoparticles, platinum (Pt) nanoparticles, quantum dots, upconversion nanoparticles (UCNP), a graphene-nanoparticle complex, a color-dyed particles and latex nanoparticles.

In one exemplary embodiment of the present invention, Dynabead (MyOne Streptavidin C1) is used as nanoparticles, and other than this, magnetic beads, metal particles, quantum dots, metal particles, quantum dots, upconversion nanoparticles, a graphene-nanoparticle complex, color-dyed particles or latex nanoparticles, which can be treated to capture a nucleic acid on the surface thereof, may be used. Preferably, magnetic beads or metal particles may be used.

The nanoparticles of the present invention are coated with any one selected from the group consisting of avidin, amines, streptavidin, which can capture a nucleic acid on a surface thereof, an antibody binding to a primer-binding antigen through an antigen-antibody reaction (e.g., a digoxigenin/anti-digoxigenin antibody, a Cy3/anti-Cy3 antibody or an equivalent thereof), an aptamer and an oligonucleotide.

To amplify a target nucleic acid, a primer including an antigen is used, and when an antibody against the antigen binds to the surface of nanoparticles, the nanoparticles may capture a target nucleic acid through the antigen-antibody reaction.

The component generating a density difference acts to support the underlying gel component, and is precipitated when a density of the nucleic acid-nanoparticle complex is higher than that of the component generating a density difference. When a density of the nucleic acid-nanoparticle complex is lower than that of the component generating a density difference, the component generating a density difference acts to separate the nucleic acid-nanoparticle complex into each component to prevent precipitation such that a negative or positive determination can be made using a density difference. Therefore, a separate washing or separation step is not required.

The component generating a density difference of the present invention may be any material capable of generating a density difference without limitation, preferably any one selected from the group consisting of glass beads, a quartz-based matrix, Percoll, colloidal silica media, and Ficoll, and more preferably glass beads.

The gel component of the present invention may be any one selected from the group consisting of IgG-agarose, agarose, agar, cellulose acetate and a polyacrylamide gel, and preferably IgG-agarose or agarose.

In one exemplary embodiment of the present invention, IgG-agarose is used, and when 10 to 30 µl, preferably 15 to 25 µl, and more preferably 20 µl of the IgG-agarose is used, a positive or negative determination may take the least time, and a high distinction ability may be exhibited.

The kit for detecting a nucleic acid of the present invention may further include an intercalating agent, such as an enhancer. Due to the addition of the enhancer, there is an effect of more clearly determining positive or negative, and the intercalating agent may be, but is not limited to, SYBR green, ethidium bromide, Biotium's GelRed, Biotium's Gel-Green, the JOJO series, POPO series, SYTO series, BOBO series, TOTO series, actinomycin, adriamycin, anthracene, benzopyrene, propidium diiodide-intertwining, distamycin, netropsin and acridine, psoralen, berberine, proflavine, daunomycin, doxorubicin, thalidomycin, a cyanin dye or LDS 751. The intercalating agent is preferably any one selected from the group consisting of intercalating dyes including SYBR green, ethidium bromide, Biotium's Gel-Red, Biotium's GelGreen, the JOJO series, POPO series, SYTO series, BOBO series and TOTO series.

The kit for detecting a nucleic acid of the present invention is an in situ kit for detecting a nucleic acid, which includes a primer set preferably consisting of a biotin-labeled forward primer and a fluorescence-labeled reverse primer, and specifically binding to a nucleic acid to be detected; capture nanoparticles; an intercalating agent; and a gel card in which a component generating a density difference and a gel component are sequentially stacked.

The present invention provides a detectable nanoparticle complex including target nucleic acid-capturing or binding nanoparticles to be used in an assay for detecting a target nucleic acid.

The present invention provides a gel card in which a glass bead component and a gel component are sequentially stacked to detect a nanoparticle complex.

The gel card in which the glass bead component and the gel component are stacked is configured to be contained in a test container, which can be any solid container, and can be processed into different types. For example, any container such as a test tube or a microplate well can be used.

The inventors provides a method for detecting a nucleic acid, which includes (a) amplifying a target nucleic acid using a primer set specifically binding to a target nucleic acid; (b) adding nanoparticles to the amplified nucleic acid obtained in Step (a) to allow the nucleic acid to be captured by or bind to the nanoparticles; (c) putting the complex obtained by capturing the nucleic acid by the nanoparticles or binding the nucleic acid to the nanoparticles as described in Step (b) into a gel card container; (d) centrifuging the mixture prepared in Step (c); and (e) comparing a location of a precipitate in the gel card container with a control.

The primer set may include a biotin-labeled forward primer and a fluorescence-labeled reverse primer. A primer included in the kit for detecting a nucleic acid of the present invention may be labeled with biotin, and the biotin-labeled primer is used to easily detect a nucleic acid since it is more easily captured by or bound to nanoparticles.

Preferably, the primer set may include a biotin-labeled forward primer and a Cy3-labeled reverse primer.

The biotin-labeled forward primer may bind to nanoparticles coated with a substance specifically binding to biotin (e.g., avidin, etc.), and the position of a precipitate may be identified using a Cy3-labeled reverse primer through visual or fluorescence analysis. In addition, Cy3 also acts as an enhancer capable of more clearly identifying an amplified product.

In an exemplary embodiment of the present invention, an HPV nucleic acid is detected using a primer set represented by SEQ ID NOs: 1 and 2 or a primer set represented by SEQ ID NOs: 3 and 4.

The nucleic acid of the present invention includes DNA and RNA, and DNA amplification can be performed by any method conventionally known in the art, and preferably, PCR or an isothermal amplification method. In addition, for RNA amplification, any method, preferably, a method for amplifying cDNA after synthesis, and more preferably, reverse transcription PCR (RT-PCR), conventionally known in the art is used.

In the present invention, step (a) is a step of amplifying a nucleic acid by PCR or an isothermal amplification reaction.

The nucleic acid of the present invention may include DNA and RNA, and the DNA may be amplified by any method conventionally known in the art, and preferably, PCR or an isothermal amplification reaction.

The isothermal amplification reaction of the present invention may be performed by any one method selected from the group consisting of HDA, RPA, RCA, LAMP, NASBA, TMA, SMART, SDA, IMDA, SPIA and cHDA.

PCR is a fast analysis method with excellent selectivity, but a temperature should be changed periodically during the reaction. A technique in which DNA/RNA amplification is isothermally performed without a temperature change is an isothermal amplification technique. Since the isothermal amplification technique does not need time for temperature change, a great quantity of DNA can be amplified within a short time, thus it is highly applicable as a fast detection technique for a nucleic acid. Representatively, loop-mediated isothermal amplification (LAMP) is a technique for amplifying a specific target sequence using 4 to 6 primers, and when magnesium pyrophosphate or SYBR green is added, nucleic acid amplification can be determined visually after amplification, and therefore it will be very highly applicable in rapid point-of-care detection technology.

NASBA and TMA are amplification methods in which cDNA is synthesized using an RNA template, and then RNA is synthesized by a self-sustained reaction, and these procedures are repeated. SMART is a target-dependent method for detecting target DNA or RNA by amplification without a temperature change. SDA is a method which needs four primers, uses a restriction enzyme, and applies a recognition base sequence (GTTGAC) of Hinc. RCA is a method for circularly elongating a primer by a Φ29 DNA polymerase, thereby amplifying a circular nucleic acid with a high molecular weight into a long strand. RCA is used as an important fundamental technique for DNA diagnosis among other isothermal amplification techniques due to strong bonds. RCA, as a recent noticeable method, is currently used in immunoassays, sequencing, SNP scoring and gene expression analysis as well as genetic testing. IMDA is a method for elongation performed by attaching primers at both sides of a double-stranded nucleic acid. HDA is a method for DNA amplification that takes place at a constant temperature without a need for denaturation time, by separating DNA into single strands using a helicase. SPIA is an amplification method using a DNA polymerase, which synthesizes cDNA from RNA, removes the RNA using RNase H and attaches a primer for SPIA. According to a continuous amplification reaction between the SPIA primer and the polymerase, several strands are generated from one strand of cDNA. cHDA is a method that takes place at a constant temperature using both a DNA polymerase and a helicase.

In one exemplary embodiment of the present invention, a nucleic acid is detected through amplification by HDA and RPA reactions, an LAMP or RCA reaction is also one of amplification reactions suitable for point-of-care molecular diagnostics, and the isothermal amplification reaction of the present invention is preferably HDA, RPA, RCA and LAMP, and more preferably HDA and RPA.

In addition, for RNA amplification, any amplification method conventionally known in the art may be used, and an NASBA reaction using RNA as a template or an RT-PCR reaction for amplification after cDNA synthesis, is preferably used.

The nanoparticles may be any nanoparticles which are able to capture or bind to a nucleic acid without limitation. Any nanoparticles that can be coated or bound with a material capable of capturing a nucleic acid may be applied.

However, since the present invention makes a positive or negative determination of a specific nucleic acid using a density difference, the density of nanoparticles should have a difference from that of a medium. In one exemplary embodiment of the present invention, as the medium, glass beads are used. The glass beads have a medium density of 1.04 g/μl, and any particles having a higher density than this can be used. However, a medium having a different density or particles having a smaller density than that of a medium may be applied.

The nanoparticles of the present invention are preferably magnetic beads, gold (Au) nanoparticles, silver (Ag) nanoparticles, platinum (Pt) nanoparticles, quantum dots, upconversion nanoparticles (UCNP), a graphene-nanoparticle complex, color-dyed particles or latex nanoparticles.

In one exemplary embodiment of the present invention, as nanoparticles, Dynabead (MyOne Streptavidin C1) is used, and other than this, magnetic beads, metal particles, quantum dots, upconversion nanoparticles, a graphene-nanoparticle complex, color-dyed particles or latex nanoparticles, which can be treated to capture a nucleic acid on a surface of the nanoparticles, may be used. More preferably, magnetic beads or metal particles are used.

A surface of the nanoparticles of the present invention may be coated with any one selected from the group consisting of avidin, amine and streptavidin, which are able to capture a nucleic acid, an antibody (e.g., an equivalent such as a digoxigenin/anti-digoxigenin antibody, a Cy3/anti-Cy3 antibody, etc.), which is able to bind to a primer-binding antigen through an antigen-antibody reaction, an aptamer and an oligonucleotide.

When a target nucleic acid is amplified, an antigen-containing primer is used, and an antibody against the antigen binds to a surface of the nanoparticles, the nanoparticle may capture a target nucleic acid by an antigen-antibody reaction.

The gel component of the present invention may be any one selected from the group consisting of IgG-agarose, agarose, agar, cellulose acetate and a polyacrylamide gel.

In one exemplary embodiment of the present invention, IgG-agarose is used, and when 10 to 30 μl, preferably 15 to 25 μl, and more preferably 20 μl of the IgG-agarose is used, a positive or negative determination may take the least time, and a high distinction ability may be exhibited.

In the present invention, in step (c), an enhancer of the intercalating agent may be additionally treated.

To clearly determine positive or negative, in the present invention, an enhancer may be additionally treated, and the enhancer may be an intercalating agent, which may be any one selected from the group consisting of SYBR green, ethidium bromide, Biotium's GelRed, Biotium's GelGreen, the JOJO series, POPO series, SYTO series, BOBO series, TOTO series, actinomycin, adriamycin, anthracene, benzopyrene, propidium diiodide-intertwining, distamycin, netropsin and acridine, psoralen, berberine, proflavine, daunomycin, doxorubicin, thalidomycin, a cyanin dye and LDS 751, and preferably, any one selected from the group consisting of intercalating dyes including SYBR green, ethidium bromide, Biotium's GelRed, Biotium's GelGreen, the JOJO series, POPO series, SYTO series, BOBO series and TOTO series.

Figure 5:
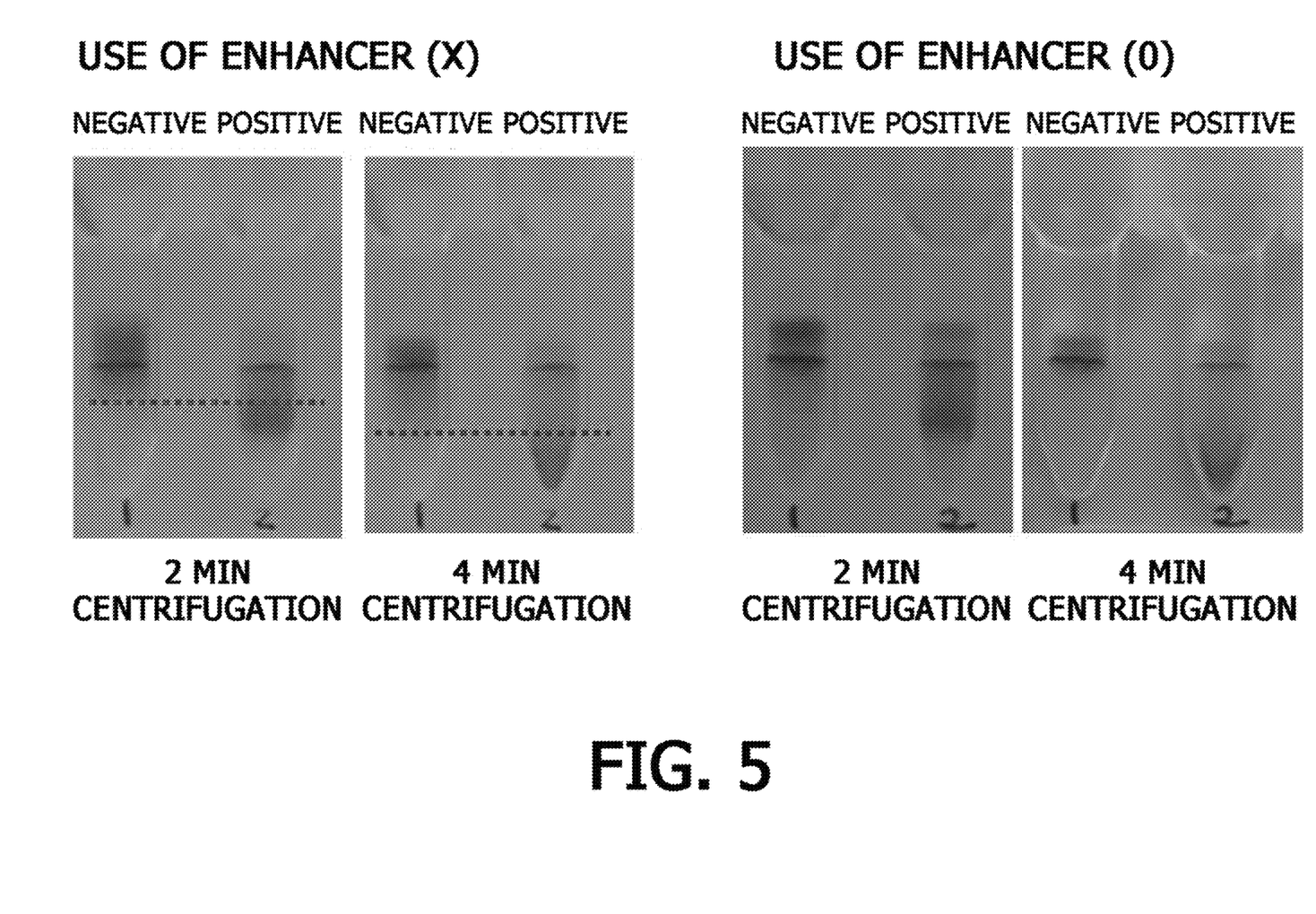
FIG. 5 shows nucleic acid detection results depending on the use of an enhancer.

In one exemplary embodiment of the present invention, GelRed (10,000×, Biotium) as an enhancer and nanoparticles are mixed with an amplified nucleic acid, and then a gel card is treated therewith. As a result, as shown in FIG. 5, when the enhancer is treated, an effect that the distinction between positive and negative became clear may be confirmed.

Meanwhile, as well as an intercalating agent, a fluorescent dye may bind to a primer and may be used as an enhancer. Any fluorescent dye that can bind to a primer is possibly used, and examples of the fluorescent dye include Cy3, Cy5, TAMRA, TEX, TYE, HEX, FAM, TET, JOE, MAX, ROX, VIC, Cy3.5, Texas Red, Cy5.5, TYE, BHQ, Iowa Black RQ, the IRDye series and equivalents thereof.

In the step of comparing a location of the precipitate in the container with a control, in the case of using a primer fluorescence-labeled by NHS modification, when the precipitate in the container is located at a lower position compared to a negative control, it may be determined as positive, and when located at a position similar to the negative control, it may be determined as negative. FIG. 2 is a schematic diagram of the present invention, and when a target nucleic acid is included in a specimen, after a target nucleic acid is captured by nanoparticles, the nucleic acid settles through centrifugation using a density difference. However, when the target nucleic acid is not included, a density is relatively low since there is no binding with nanoparticles, a precipitate is located at the middle of a tube.

However, in the case of the use of a primer fluorescence-labeled by phosphoramidite synthesis, when the precipitate in the container is located at a lower position compared to the negative control, it may be determined as negative, and when located at a position similar to the negative control, it may be determined as positive. The experimental results related thereto are shown in FIG. 3.

The present invention does not include separation and washing steps before Step (d).

The prior art document, U.S. Patent Application Publication No. 2014-0100131, relates to a method for detecting a target gene, the method using magnetic beads and a capturing antibody, and detecting a target gene through separation. In addition, the prior art document, U.S. Patent Application Publication No. 2010-000938, also uses magnetic beads and a capturing antibody, and may detect a target biomolecule through separation. However, the present invention does not have a limitation on particles, and may more easily, simply and rapidly detect a target nucleic acid since an antibody may not be used, and separation and washing are not needed.

The present invention is for identifying the presence of a nucleic acid in multiple ways by treating two or more primers labeled with different colors of fluorescence in step (a) of the present invention.

In the step of amplifying a nucleic acid, the presence of a nucleic acid may be identified in multiple ways by treating two or more primers labeled with different colors of fluorescence. Therefore, the presence of multiple nucleic acids may be determined through only one experiment, and thus it is effective method for detecting a nucleic acid because time and costs are saved.

EXAMPLES

Hereinafter, the present invention will be described in further detail with reference to examples. There examples are merely provided to explain the present invention in further detail, and therefore, according to the inventive concept, it is obvious to those of ordinary skill in the art that the scope of the present invention is not limited by the examples.

Example 1

Genomic DNA Extraction from Sample and Amplification

To extract genomic DNA from a cervical specimen, a nucleic acid was extracted according to manufacturer's protocols using a nucleic acid extraction kit (QIAamp DNA Micro kit, QIAGEN, Valencia, Calif., USA or ChargeSwitch gDNA 1 μl Serum Kit, Life Technologies, NY, USA), and a nucleic acid was prepared by requesting the Ministry of Food and Drug Safety and National Institute for Biological Standards and Control (NIBSC) to provide a human papilloma virus (HPV) DNA standard.

TABLE 1

Primer information

| | Sequences of primers (5'→3') | Size of fragment (bp) | SEQ ID NO: |
|---|---|---|---|
| Forward | 5'-biotin-TTGTTGGGGTAACCAACTATTTGTTACTGTT | 136 | 1 |
| Reverse | 5'-Cy3-CCTCCCCATGTCTGAGGTACTCCTTAAAG | | 2 |
| Forward | 5'-biotin-TGTCAGAACCATATGGCGACAGCTT | 95 | 3 |
| Reverse | 5'-Cy3-TTCACCAACAGCACCAGCCCTATTA | | 4 |

An amplification product for each specimen was obtained using the PCR primer set listed in Table 1. The primer set of the present invention was manufactured to facilitate isothermal amplification (preferably, helicase dependent amplification (HDA), recombinase polymerase amplification (RPA)) as well as PCR amplification, and modified with reference to a conventionally known document (Virol J. 2010 Aug. 19; 7:194).

TABLE 2

PCR reaction mixture composition

| Components of PCR | Volume |
|---|---|
| Forward/reverse primer (10 pmole/μl) | 1 μl |
| HotStarTaq plus Master Mix | 10 μl |
| Template DNA (1 ng/μl) | 5 μl |
| Deionized water | 4 μl |
| Total | 20 μl |

TABLE 3

RPA reaction mixture composition

| Components of PCR | Volume |
|---|---|
| Forward/reverse primer (10 pmole/μl) | 3 μl |
| Rehydration buffer | 29.5 μl |
| Template DNA (1 ng/μl) | 5 μl |
| Deionized water | 11.5 μl |
| $Mg^{2+}$ | 1 μl |
| Total | 50 μl |

TABLE 4

RPA reaction mixture composition

| Components of PCR | Volume |
|---|---|
| Forward/reverse primer (10 pmole/μl) | 3 μl |
| 10X reaction buffer (tris-HCl; pH 9.0, $(NH_4)_2SO_4$ | 2.5 μl |
| IsoAmp III tHDA master mix | 25 μl |
| IsoAmp enzyme mix | 2 μl |
| Template DNA (1 ng/μl) | 5 μl |
| Deionized water | 16.5 μl |

TABLE 4-continued

RPA reaction mixture composition

| Components of PCR | Volume |
|---|---|
| $MgSO_4$ | 1 μl |
| NaCl | 2 μl |
| Total | 50 μl |

1) PCR

A PCR reaction mixture composition was shown in Table 2, and amplification was performed under conditions of 95° C. for 10 minutes, and 40 cycles of [95° C. for 30 seconds, 55° C. for 30 seconds, and 72° C. for 30 seconds].

2) RPA

An RPA reaction mixture composition was shown in Table 3, isothermal amplification was performed using the primer sets listed in Table 1 and a TwistAmp basic kit (TwistDx, Cambridge, UK) at 37° C. for 40 minutes.

3) HDA

An HDA reaction mixture composition is shown in Table 4, and isothermal amplification was performed using the primer sets listed in Table 1 and an IsoAmp III Universal tHDA kit (Biohelix) at 65° C. for 60 minutes.

Example 2

Identification of Amplification Product by Electrophoresis

PCR products were analyzed by a Mupid-a (Advance, Japan) electrophoresis device using 1.5% (w/v) agarose gel. 1.5 g of agarose was put into an Erlenmeyer flask (250 μl), filled with 100 μl of a 0.5× tris boric acid EDTA (TBE) buffer solution, dissolved for 2 to 3 minutes in a microwave oven, and then the resulting solution was poured into a gel container and solidified for approximately 30 minutes. After confirming that the gel was completely solidified, the gel was collected. The collected gel was loaded in an electrophoresis device, and charged with a 0.5×TBE buffer solution. In addition, 4 μl of a PCR product and 0.8 μl of a 6× bromophenol blue (BPB) dye were mixed to load 4 µl, and then subjected to electrophoresis at 100 V for 25 minutes. Afterward, the gel was detached, stained with ethidium bromide (EtBr) for 10 minutes, and washed with distilled water for 10 minutes to remove non-DNA-binding EtBr. Finally, the agarose gel was plated on a UV transilluminator to analyze a PCR amplification result.

As a result of carrying out electrophoresis on the PCR amplification product, a 136-bp band was identified, and it was confirmed that target DNA was normally amplified according to the method described in Example 1 (the result not shown).

Example 3

3-1. Preparation of Nanoparticles and Gel Card

Theoretically, all nanoparticles are usable as long as they can capture a nucleic acid and have a higher density than a medium. In Example 3, to capture a nucleic acid molecule, as nanoparticles, Dynabead (MyOne Streptavidin C1) was used. A surface of the Dynabead was treated with streptavidin, and thus bound to a biotin-labeled primer. In addition, as a gel card, a product of a polyspecific Ortho BioVue System (Ortho Clinical Diagnostics, NJ, USA) was purchased.

3-2. Detection of Nucleic Acid Using Primer Labeled by NHS Modification

An HPV nucleic acid was amplified from an HPV specimen through isothermal amplification using a primer set consisting of SEQ ID NOs: 1 and 2 listed in Table 1. The primer represented by SEQ ID NO: 2 was labeled with a Cy3 fluorescent substance at the 5'-end through NHS modification. The primer labeled by the NHS modification may be represented by Formula 1 below.

[Formula 1]

4 µl of the amplified nucleic acid was mixed with 4 µl of Dynabead, and put into a gel card to allow a reaction at 37° C. for 5 minutes, followed by centrifugation for 2 to 4 minutes. FIG. 2 is a schematic diagram illustrating the above process, and as a result, as shown in FIG. 2, it can be seen that a PCR product shows a band at a lower side of a nucleic acid-detected (positive) gel card, and it can be confirmed that a band is shown at an upper side of a nucleic acid-free (negative) gel card.

3-3. Detection of Nucleic Acid Using Primer Labeled by Phosphoramidite Synthesis An HPV nucleic acid was amplified from an HPV specimen through isothermal amplification using the primer set consisting of SEQ ID NOs: 3 and 4 listed in Table 1. The primer represented by SEQ ID NO: 4 was labeled with a Cy3 fluorescent substance at the 5'-end through phosphoramidite synthesis. The primer labeled by phosphoramidite synthesis is represented by Formula 2 below.

[Formula 2]

4 μl of the amplified product was mixed with 4 μl of Dynabead, and put into a gel card to allow a reaction at 37° C. for 5 minutes, followed by centrifugation. Here, migration was observed 2, 4 and 6 minutes after the electrophoresis. As a result, as shown in FIG. 3, it can be confirmed that a band was detected at a lower side in the case of the first tube containing a negative specimen, and a band was detected at an upper side in the case of the second tube containing a positive specimen.

Accordingly, the method for detecting a nucleic acid using nanoparticles of the present invention can rapidly and sensitively detect a nucleic acid from a clinical specimen, and a negative/positive determination method may be easily changed depending on a fluorescent-labeling method.

Example 4

Optimization of Nucleic Acid Detection Method
1) Centrifugation Speed
To measure the optimized centrifugation speed for detecting a nucleic acid, a gel card was treated with a nucleic acid and nanoparticles according to the method described in Example 3-2. Afterward, centrifugation was performed at each of 100 rpm, 200 rpm, 400 rpm, 600 rpm, 800 rpm, 1200 rpm and 1600 rpm for 2 minutes.

As a result, it was confirmed that 600 to 1200 rpm is the optimal range of the centrifugation speed for detecting 136-bp HPV16 DNA, and 800 rpm×2 minutes (approximately 55 g) is the most preferable (not shown).

The centrifugation speed was optimized according to the length of a nucleic acid to be detected and the size/density of nanoparticles used herein to control a g-force.

2) Centrifugation Time
To measure the optimal centrifugation time for detecting a nucleic acid, a gel card was treated with a nucleic acid and nanoparticles according to the method described in Example 3-2. The centrifugation speed was set to 800 rpm (approximately 55 g), and observed up to 8 minutes at one-minute intervals.

As a result, as shown in FIG. 3 (only the results at 2, 4 and 6 minutes are shown), it was confirmed that a positive or negative determination can be made by only at least 2-minute centrifugation, and also by 2 to 6-minute centrifugation.

However, a positive or negative determination was not clearly made by more than 6-minute centrifugation.

The centrifugation time of the present invention was able to be controlled according to the size, density and reaction amount of the nanoparticles used herein, the concentration of a medium or a centrifugal force.

3) Amount of Nucleic Acid
After the amplification of the nucleic acid according to Example 1, the gel card prepared in Example 3 was treated with 2 to 6 μl (most preferably, 4 μl) of the product amplified in the produced master mix to detect a nucleic acid. When a very small amount of nucleic acid was treated, the amount of nucleic acid binding to the nanoparticles was small, bands were not clearly formed, and therefore it was difficult to detect a band for determining positive or negative.

The amount of a nucleic acid used for treating the gel card in the detection of the nucleic acid using a gel card of the present invention was able to control an amount of the amplified product according to the type and amount of the nanoparticles reacting therewith, and the entire master mix was also able to be used.

4) Amount of Agarose
To measure the optical amount of agarose in the gel card for detecting a nucleic acid, a gel card in which each of 5 μl, 10 μl, 20 μl, 30 μl, 40 μl and 50 μl of agarose (anti-mouse IgG agarose) was stacked was treated with the PCR amplification product obtained by the method described in Example 1 and nanoparticles.

As a result, when 10 to 30 μl of agarose was included, a minimum time and high distinction ability were exhibited in making a positive or negative determination. The gel card containing 20 μl of agarose was more preferably used (not shown).

5) Addition of Enhancer
In positive or negative determinations, for clearer distinction, an enhancer may be added.

Figure 4:
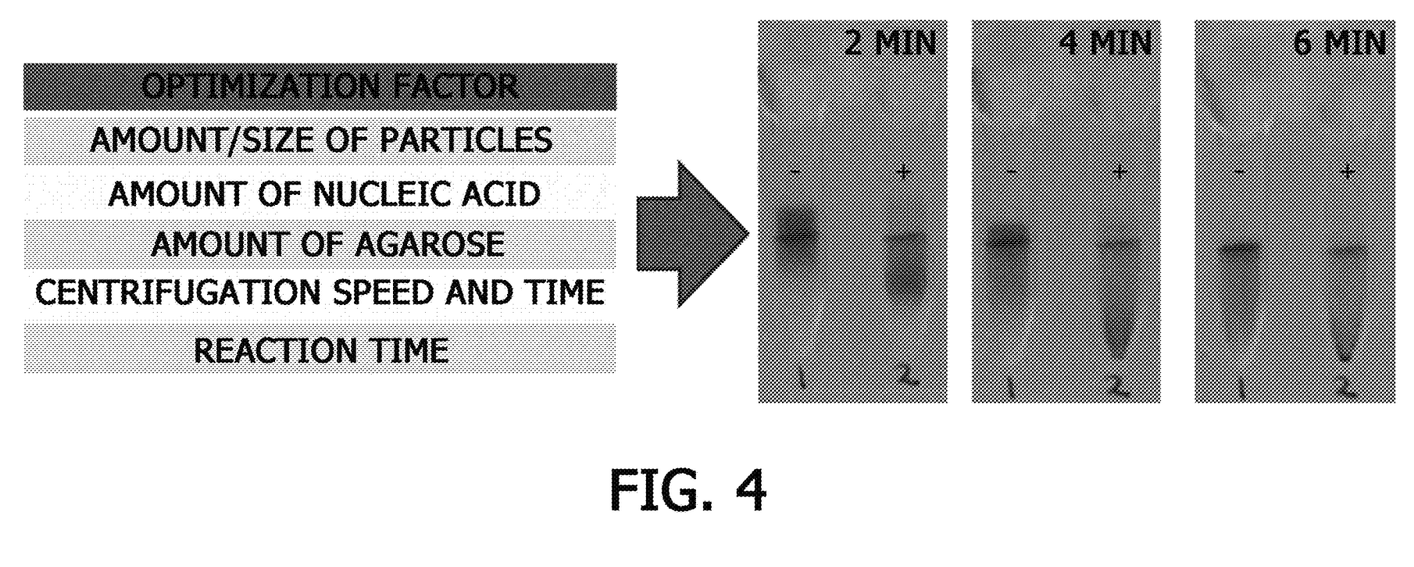
FIG. 4 shows nucleic acid detection results according to centrifugation time.

First, 1/100 1 μl of GelRed (10,000×, Biotium) as an enhancer and nanoparticles were mixed with the nucleic acid amplified by the method of Example 1, and then a gel card was treated with the resulting mixture. As a result, as shown in FIG. 4, when the enhancer was treated, it was confirmed that there is an effect of more clearly determining positive or negative (refer to FIG. 5).

Second, a fluorescent Cy3-labeled primer was used as an enhancer to amplify a nucleic acid, and then the amplified product was mixed with nanoparticles to treat a gel card. In this case, a positive or negative determination can be made by visual observation and fluorescence analysis, and the detection result becomes more apparent (refer to FIG. 6).

Example 5

Measurement of Nucleic Acid Detection Sensitivity

HPV16 DNA standards (WHO International Standard 1st WHO International Standard for Human Papilloma Virus (HPV) Type 16 DNA, $10^7$ copies/µl) were diluted to prepare $10^2$, $10^3$, $10^4$ and $10^5$ copies/µl, and then amplified by PCR.

Whether the amplified product was properly diluted was observed by the method described in Example 2, and the result was shown in FIG. 7A. 4 µl of the amplified product was mixed with 4 µl of Dynabead, the resulting mixture was put into a gel card to which 20 µl of anti-mouse IgG agarose 1/50 was added to allow a reaction at 37° C. for 5 minutes, followed by centrifugation. Here, migration was observed 2, 4, and 6 minutes after the centrifugation (FIG. 7B).

Figure 7:
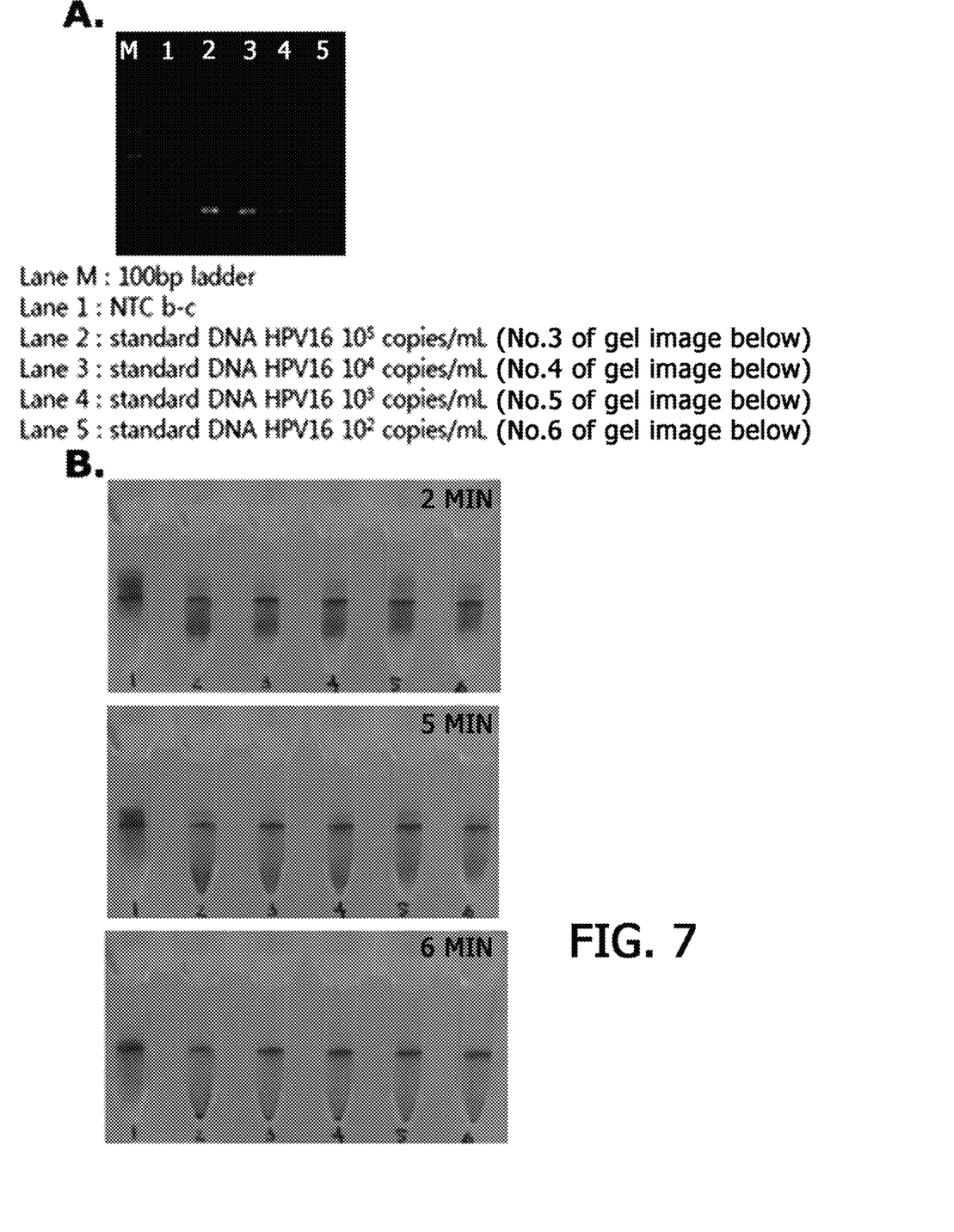
FIG. 7 shows the results of measuring detection sensitivity according to DNA concentration.

As a result, as shown in FIG. 7, it was confirmed that at all concentrations of $10^2$ to $10^5$ copies/µl, the presence of a nucleic acid can be determined as positive or negative. That is, with only $10^2$ copies/µl of a nucleic acid, the nucleic acid was able to be detected.

Example 6

Detection of Nucleic Acid from HPV Clinical Specimen

To confirm whether a nucleic acid is sensitively and specifically detected from an HPV clinical specimen, for a cervical cancer screening test, a specimen subjected to an HPV DNA test was used, and nucleic acid detection was performed using the remaining specimens. Three each of HPV DNA-positive and negative specimens were selected from specimens subjected to the Roche Cobas 4800 HPV test.

As described in the examples, from a total of six HPV specimens, HPV nucleic acids were amplified using the primer set consisting of SEQ ID NOs: 1 and 2 listed in Table 1. The primer represented by SEQ ID NO: 2 was labeled with a fluorescent substance of Cy3 at the 5'-end through NHS modification.

Afterward, 4 µl of the amplified product was mixed with 4 µl of Dynabead, and put into a gel card to which 20 µl of anti-mouse IgG agarose 1/50 was added to allow a reaction at 37° C. for 5 minutes, followed by centrifugation. Here, migration was observed 2, 4 and 6 minutes after the centrifugation.

Figure 8:
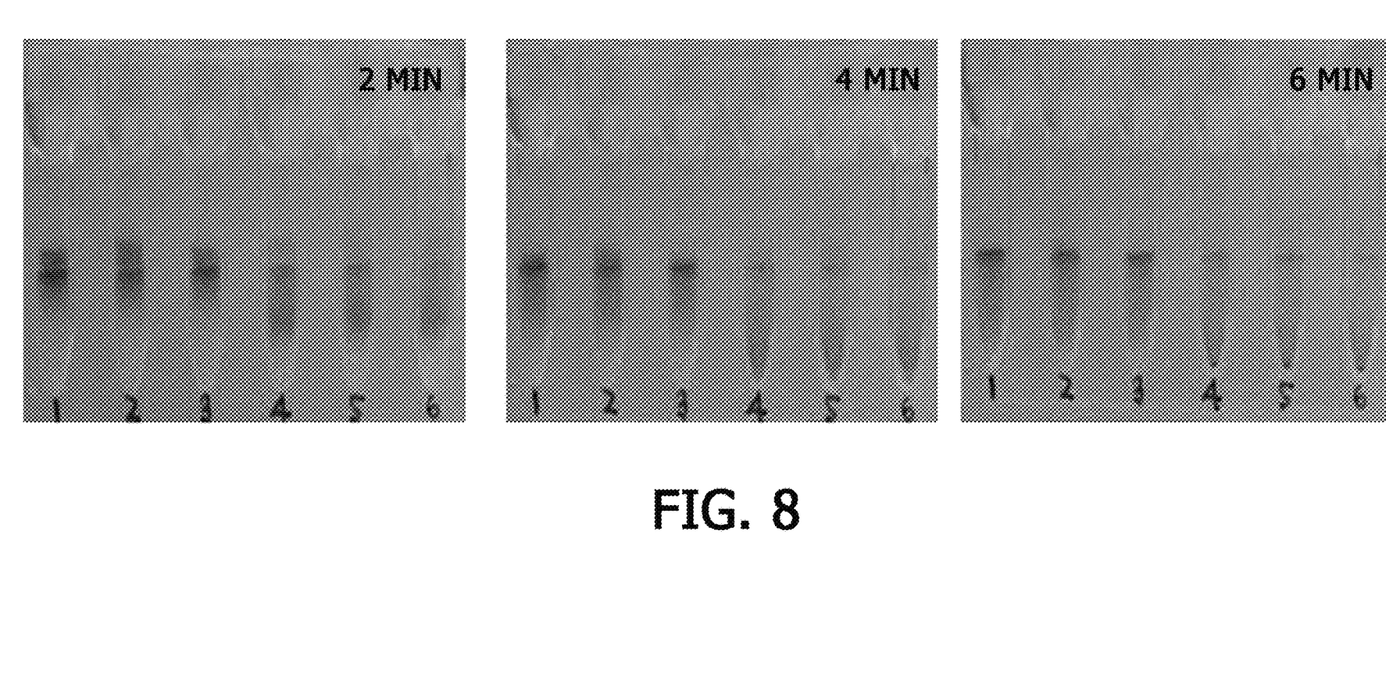
FIG. 8 shows the results of a nucleic acid detection method for HPV clinical specimens (Tubes 1 to 3: HPV DNA-negative samples, and Tubes 4 to 6: HPV DNA-positive samples).

As a result, as shown in FIG. 8, it was confirmed that a band was detected at an upper side in the case of the first and third tubes which contained negative specimens, and a band was detected at a lower side in the case of the fourth to sixth tubes which contained positive specimens. Therefore, it was confirmed that a nucleic acid can be rapidly and sensitively detected with only a clinical specimen.

INDUSTRIAL APPLICABILITY

The present invention has high industrial applicability since negative or positive determination for a specific disease can be made in a more rapid, simple, sensitive and reliable manner through a nucleic acid detection method not including a separation step.

The invention claimed is:

1. A method for detecting a nucleic acid using a difference in density of nanoparticles depending on whether the nucleic acid is captured by or binds to the nanoparticles, comprising:
   (a) amplifying a target nucleic acid using a primer set specifically binding to a target nucleic acid, wherein a forward primer is labeled with any one selected from the group consisting of biotin, an antigen, a target molecule, and an oligonucleotide, and a reverse primer is labeled with fluorescence through N-hydroxysuccinimide modification (NHS modification) or phosphoramidite synthesis;
   (b) adding nanoparticles to the amplified nucleic acid obtained in Step (a) to allow the nucleic acid to be captured by or bind to the nanoparticles, wherein the nanoparticles are coated with any one selected from the group consisting of avidin, streptavidin, an antibody, which is able to bind to a primer-binding antigen through an antigen-antibody reaction, an aptamer and an oligonucleotide complementary to the oligonucleotide labeled to the forward primer;
   (c) putting the complex obtained by capturing the nucleic acid by the nanoparticles or binding the nucleic acid to the nanoparticles as described in Step (b) into a gel card container in which a component generating a density difference and a gel component are sequentially stacked, wherein a layer comprising the gel component is above a layer comprising the component generating the density difference;
   (d) centrifuging the mixture prepared in Step (c); and
   (e) comparing a location of a precipitate in the gel card container with a control,
   wherein when a nucleic acid is detected using a primer fluorescence-labeled by NHS modification, a positive specimen shows a distribution of the precipitate at a lower side compared to a negative specimen; and
   when a nucleic acid is detected using a primer fluorescence-labeled by phosphoramidite synthesis, a positive specimen shows a distribution of the precipitate at an upper side compared to a negative specimen.

2. The method of claim 1, wherein Step (a) is a step of amplifying a nucleic acid by a polymerase chain reaction (PCR) or isothermal amplification reaction.

3. The method of claim 2, wherein the isothermal amplification reaction is performed by any one selected from the group consisting of Helicase-Dependent Amplification (HDA), Recombinase Polymerase Amplification (RPA), Rolling Circle Amplification (RCA), Loop mediated isothermal amplification (LAMP), Nucleic Acid Sequence-Based Amplification (NASBA), Transcription Mediated Amplification (TMA), Signal Mediated Amplification of RNA Technology (SMART), Strand Displacement Amplification (SDA), Isothermal Multiple Displacement Amplification (IMDA), Single Primer Isothermal Amplification (SPIA) and circular Helicase-Dependent Amplification (cHDA).

4. The method of claim 1, wherein the nanoparticles are any one selected from the group consisting of magnetic beads, gold (Au) nanoparticles, silver (Ag) nanoparticles, platinum (Pt) nanoparticles, quantum dots, upconversion nanoparticles (UCNP), a graphene-nanoparticle complex, color dyed particles and latex nanoparticles.

5. The method of claim 1, wherein the gel component is any one selected from the group consisting of IgG-agarose, agarose, agar, cellulose acetate and a polyacrylamide gel.

6. The method of claim 1, wherein Step (c) further comprises a step of treating the complex with an intercalating agent.

7. The method of claim 1, wherein, before Step (d), a separate separation or washing step is not included.

8. The method of claim 1, wherein, in Step (a), the presence of a nucleic acid is identified in multiple ways by treating two or more fluorescence-labeled primer sets with different colors.

* * * * *

SEQUENCE LISTING

```
<160> NUMBER OF SEQ ID NOS: 4

<210> SEQ ID NO 1
<211> LENGTH: 31
<212> TYPE: DNA
<213> ORGANISM: Artificial
<220> FEATURE:
<223> OTHER INFORMATION: HPV forward primer1

<400> SEQUENCE: 1
ttgttggggt aaccaactat ttgttactgt t                              31

<210> SEQ ID NO 2
<211> LENGTH: 29
<212> TYPE: DNA
<213> ORGANISM: Artificial
<220> FEATURE:
<223> OTHER INFORMATION: HPV reverse primer1

<400> SEQUENCE: 2
cctccccatg tctgaggtac tccttaaag                                 29

<210> SEQ ID NO 3
<211> LENGTH: 25
<212> TYPE: DNA
<213> ORGANISM: Artificial
<220> FEATURE:
<223> OTHER INFORMATION: HPV forward primer2

<400> SEQUENCE: 3
tgtcagaacc atatggcgac agctt                                     25
```

```
<210> SEQ ID NO 4
<211> LENGTH: 25
<212> TYPE: DNA
<213> ORGANISM: Artificial
<220> FEATURE:
<223> OTHER INFORMATION: HPV reverse primer2

<400> SEQUENCE: 4
ttcaccaaca gcaccagccc tatta                                              25
```